United States Patent [19]
Swanson et al.

[11] Patent Number: 5,707,236
[45] Date of Patent: Jan. 13, 1998

[54] SELECTIVELY SORBENT ARTICLE AND METHOD FOR USE IN DENTAL APPLICATIONS

[75] Inventors: Jerome E. Swanson, St. Paul; Kevin M. Cummings, Little Canada, both of Minn.

[73] Assignee: Minnesota Mining and Manufacturing Company, St. Paul, Minn.

[21] Appl. No.: 520,347

[22] Filed: Aug. 28, 1995

[51] Int. Cl.⁶ ............................................. A61C 5/04
[52] U.S. Cl. ................................... 433/226; 433/219
[58] Field of Search ................................. 433/218, 219, 433/228.1, 215, 226

[56] References Cited

U.S. PATENT DOCUMENTS

| | | | |
|---|---|---|---|
| 3,764,527 | 10/1973 | Sohl | 210/30 |
| 3,957,067 | 5/1976 | Ferraro | 132/89 |
| 4,784,892 | 11/1988 | Storey et al. | 428/172 |
| 4,987,632 | 1/1991 | Rowe et al. | 15/104.93 |
| 5,152,809 | 10/1992 | Mattesky | 51/295 |
| 5,230,119 | 7/1993 | Woods et al. | 15/209.1 |

FOREIGN PATENT DOCUMENTS

| | | |
|---|---|---|
| 0 277 009 | 1/1988 | European Pat. Off. |
| 0 535 451 A1 | 9/1992 | European Pat. Off. |

OTHER PUBLICATIONS

NuGauze™ Sponges product–Johnson & Johnson Medical; Patterson Dental Catalog: p. 113, (1993).

*Primary Examiner*—Nicholas D. Lucchesi
*Attorney, Agent, or Firm*—Dale A. Bjorkman

[57] ABSTRACT

The present specification describes a cleanup article which selectively sorbs hydrophobic dental resins. The article is particularly useful in the removal of excess resin-containing materials from the mouth during dental procedures. The article preferably is of sufficient integral strength to prevent break-up of the article during use.

12 Claims, 2 Drawing Sheets

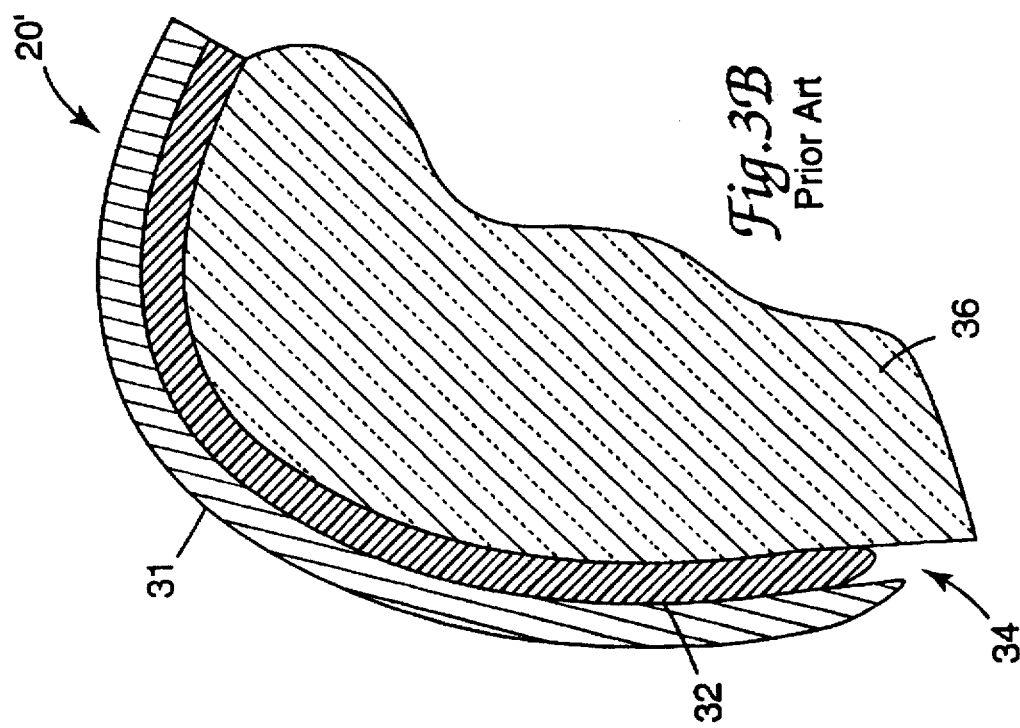
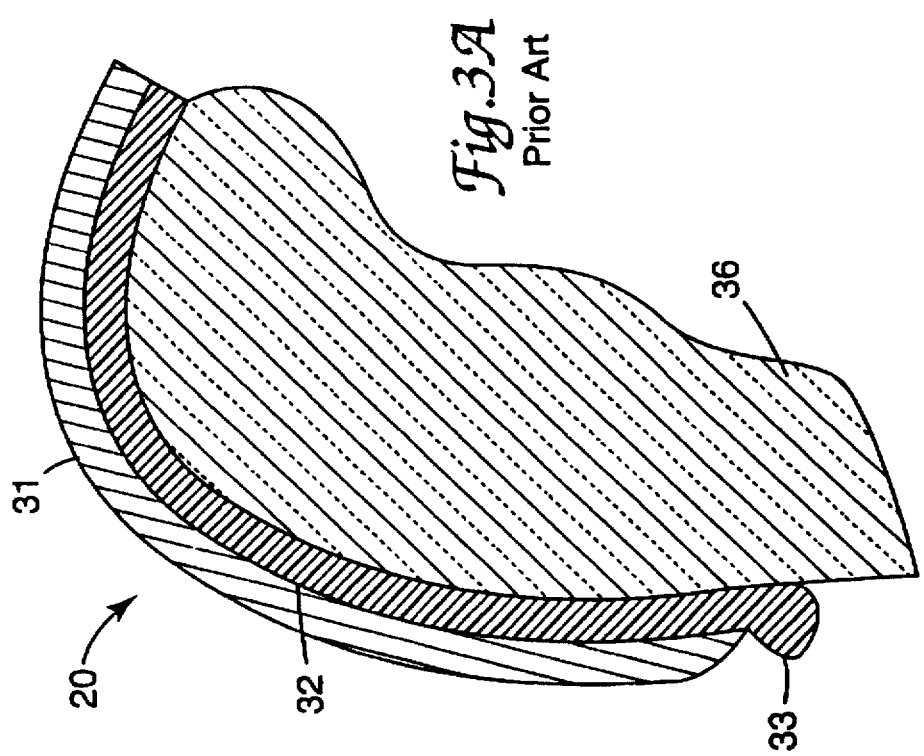

5,707,236

SELECTIVELY SORBENT ARTICLE AND METHOD FOR USE IN DENTAL APPLICATIONS

FIELD OF INVENTION

The present invention relates to an article which aids in the removal of excess resin-containing materials and a method for using such an article. The present invention provides an article and method which are particularly useful in the removal of excess resin containing materials from the mouth during dental procedures.

BACKGROUND

Materials with an absorbent inner layer and a hydrophobic barrier layer are well known in the art. See, for example, U.S. Pat. No. 4,784,892. Such a material can be used for a variety of purposes, such as for disposable protective clothing, filtration, or disposable wipes for domestic or industrial purposes. The bulk properties of these materials are geared toward absorbency, with the barrier layer the only hydrophobic portion.

Materials are well known in the art which preferentially retain a substance to the exclusion of water. U.S. Pat. No. 3,764,527 discloses an oleophilic fibrous web in which the fibers are preferentially wetted by oil in an oil-water mixture, retaining the oil in the internal voids of the web while rejecting water.

A non-sterile, general use material, NuGauze™ sponge from Johnson & Johnson, absorbs both water and resins. This material is applied by hand or by gripping a piece of the material with a cotton pliers.

SUMMARY OF THE INVENTION

A dental article is provided for use in selectively sorbing substantially hydrophobic dental resins from an environment containing aqueous fluids. The article comprises a material having a Water Repellency Value greater than 1.

BRIEF DESCRIPTION OF THE DRAWINGS

The invention will be further explained with reference to the drawing, wherein:

FIGS. 3A and 3B are prior art representing a partial cross-section respectively of a seated crown with excess cured resin-containing cement left at the margin, a seated crown with excess cured resin-containing cement chipped away, and a seated crown with excess resin-containing cement wiped away prior to cure by an embodiment of the present invention.

Figure 1:
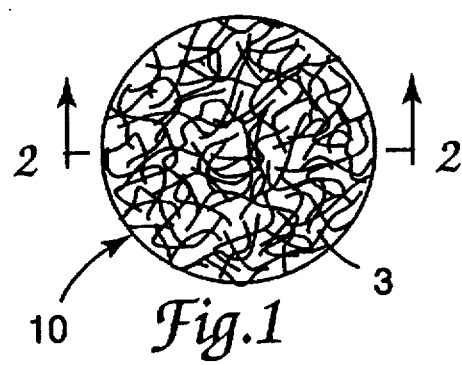
FIG. 1 is a plan view of an embodiment of the article of the invention.

These figures, which are idealized, are not to scale and are intended to be merely illustrative and non-limiting.

DETAILED DESCRIPTION OF ILLUSTRATIVE EMBODIMENTS

The need exists for an easy, efficient means of removing excess resin-containing materials from a moist environment completely and without smearing. It is desirable to have a cleanup pad capable of preferentially absorbing resin-containing materials without leaving resin on the surface which has been wiped. It is also desirable that the cleanup pad stay in one piece even when saturated. The present invention provides such a cleanup pad.

The present invention provides an article and method for the removal of excess resin-containing substances by wiping with a hydrophobic sorbent material. The cleanup pad of the invention selectively sorbs hydrophobic resins resulting in a smooth and even wiped surface that is substantially free of residual resin. These wiping pads are useful for removing excess resins during dental procedures either in the mouth or on models in the dental laboratory. The present invention is particularly useful in the removal of excess resin containing materials from the moist environment of the mouth during dental procedures, since the pad will preferentially sorb resins.

In a preferred embodiment, the article of the invention is in the form of a pad, in a size and shape suitable to be placed into the mouth without excessive bulkiness, but large enough to sorb and thus remove a substantial amount of resin-containing material. The bulk sorbent material is sufficiently hydrophobic such that the material will selectively sorb hydrophobic dental resins.

In dental procedures, such as cementing a crown in place, it is important that the clinician have an efficient and easy means of removing the excess cement. During crown seating, uncured cement must be cleaned up because exposure of the oral soft tissues to the uncured resin in the cement can result in sensitization problems for some patients. Typically in seating a crown, excess cement is expressed at the margin of the crown and is allowed to partially cure. The partially hardened cement is then removed in pieces with a dental instrument. This technique may leave an open or rough margin which may facilitate caries or periodontal disease. Alternatively, the resin-containing cement may be removed immediately after the crown is seated. Such immediate removal is typically performed with a cotton swab, which results in incomplete removal of the cement. The cotton absorbs oral cavity fluids, and consequently does not readily absorb the resinous material but instead smears it.

An advantage of the present invention over materials currently available for wiping away excess resin-containing materials such as dental cement is that the material of the present invention results in a smooth, even surface without excess cement or voids which may facilitate recurrent caries.

While the size, shape, and thickness of the pad is not critical, the clinician needs to be able to handle the pad with the fingers or with an instrument such as a cotton pliers. The pad should be of appropriate size and shape to use easily in the mouth. When using a cotton pliers, the pad is preferably in the form of a disk of about 6 millimeters to 12 millimeters diameter. Preferably, the pad has a thickness of less than about 2 millimeters. When the pad is to be handled by the fingers, it preferably has a square, rectangular or triangular shape having a side measurement of less than about 5 centimeters, or a circular elliptical or oval shape having a diameter or length of less than about 5 centimeters. Other shapes, such as hexagonal, star-shaped, letter shapes, random shapes and the like are also contemplated. Preferably, the article of the present invention has a sheet-like configuration having an overall size of less than about 250 cm². More preferably, the article has an overall size of less than about 25 cm².

Figure 2:
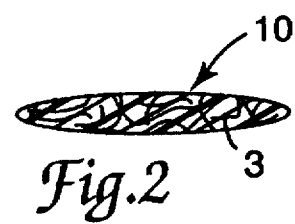
FIG. 2 represents a cross-sectional view along line 2—2 of FIG. 1.

FIG. 1 depicts an embodiment of the invention 10 where 3 is an individual fiber. The pad is typically conveyed to the mouth with a cotton pliers. FIG. 2 is a cross-sectional view of FIG. 1 taken along line 2—2 of FIG. 1.

Figure 5:
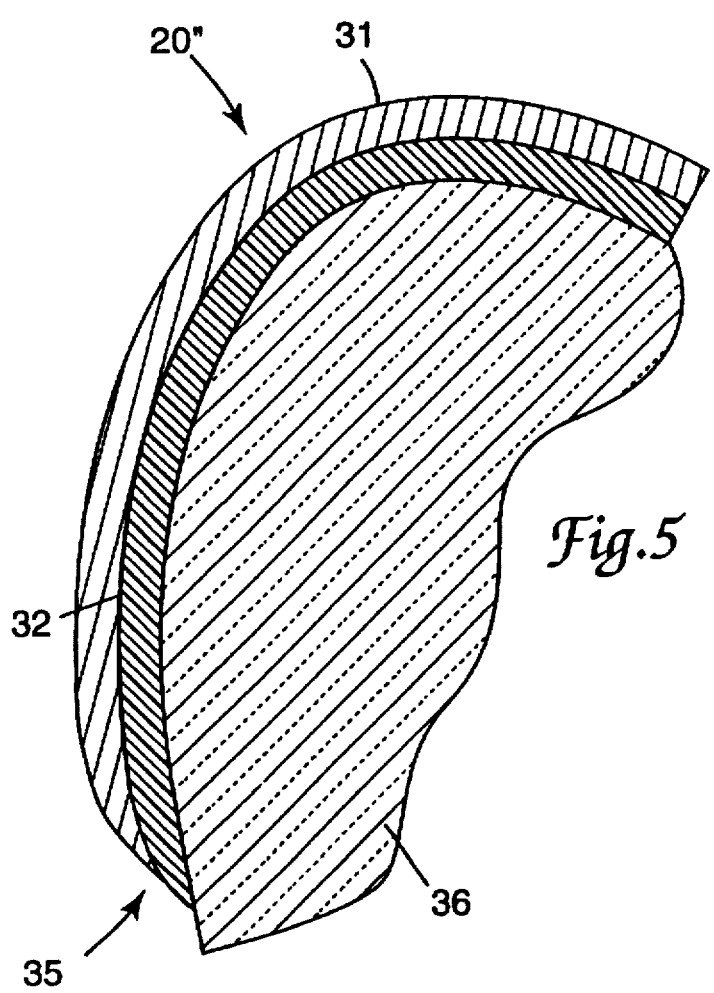
FIG. 5 is a partial cross-section of the invention showing the excess resin-containing cement wiped away.

FIG. 3A depicts a cemented crown and tooth combination 20. Crown 31 is cemented to a prepared tooth 36. Prior to seating, the crown 31 is lined with a cement 32. When the crown is seated onto the prepared tooth, the excess cement squeezes out at the margins. Overhang 33 results from incomplete removal of excess cement. If unremoved, the overhang may facilitate periodontal disease. Typically, such overhangs are removed with a dental instrument such as an explorer, which may result in an open margin. FIG. 3B depicts a crown and tooth combination 20', where 36 is the prepared tooth, 31 is the crown, 32 is the cement, and 34 is an open margin resulting from the partially hardened cement being removed. Such an open margin may lead to caries or periodontal disease. FIG. 5 depicts a cemented crown and tooth combination 20", where 36 is the prepared tooth, 31 is the crown, 32 is the cement, and 35 is a smooth wiped surface. There is typically a gap of about 50 to 150 micrometers between the crown and the tooth that should be filled with cement.

Figure 4:
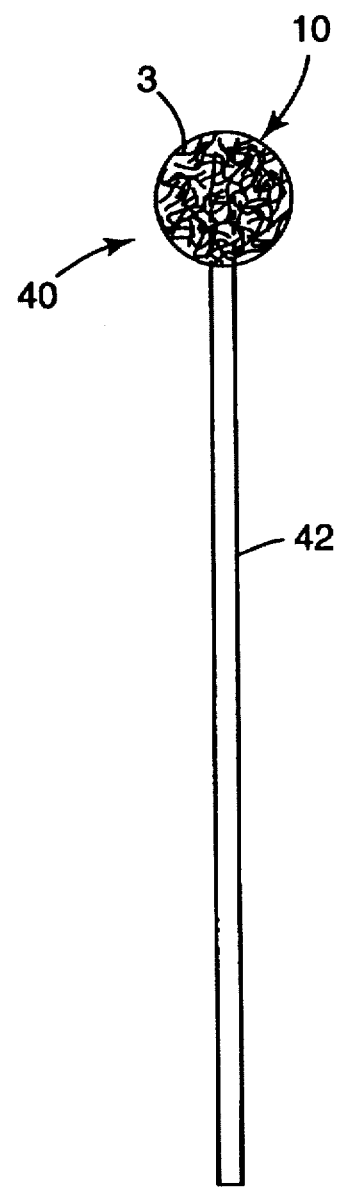
FIG. 4 represents a plan view of an embodiment of the invention wherein the pad is attached to a carrier to facilitate use of the cleanup pad.

FIG. 4 depicts an embodiment of the invention 40, having carrier 42 such as a wood or plastic applicator to which the pad 10 or pad material is attached. The carrier 42 serves as a means to convey the pad 10 to the place where it will be used, such as the tooth or the model.

The fibers of hydrophobic resinophilic material comprising the pad are of appropriate fiber diameter and density to absorb or adsorb a substantial amount of resin. Another important aspect of the fibers is surface area which is inversely related to the square of the fiber diameter.

Fiber diameters and pad densities may be varied within a considerably wide range. It will be apparent to those skilled in the art that the lower the density of the pad, the more readily the pad will sorb and retain large amounts of resin. The size of the interstices influences the entrapment and retention of resin in the interstitial spaces, rather than sorption of the resin as a film on the surface of the fibers.

Any suitable fibers which exhibit the desired characteristics may be used to form the web from which the pads are made. A particularly preferred material from which to form the pad is a polypropylene blown micro-fiber web as described in U.S. Pat. No. 3,764,527 (Sohl).

Other suitable materials include polyethylene or a blend of polypropylene and polyethylene. The material selected must preferentially sorb resin. The material selected should be sufficiently hydrophobic so that the pad does not sorb a quantity of water such that it will interfere with the sorption of the resin and smear the resin.

The preferred pad materials may be defined broadly as those materials (usually polymeric) which when contacted with a resin-water mixture, allow the resin to displace water from a smooth surface thereof and to form a contact angle with said surface of less than 90 degrees. Generally, the effectiveness of the fiberforming material has an inverse relationship to the size of the above described contact angle. Thus, polypropylene and polyethylene surfaces allow resin to assume a contact angle of substantially zero degrees and therefore fibers of these polymers provide the preferred materials for practicing the invention.

An important physical property of material comprising the wipe is hydrophobicity, measured as a bulk property. The material comprising the cleanup pad of the invention is preferentially wetted by resin and selectively sorbs dental resin.

Currently used materials such as cotton swabs or gauze are hydrophilic. These materials sorb water, becoming saturated so that they cannot effectively sorb resin. Consequently, these materials merely smear the resin instead of sorbing it. Thus, the currently used cleanup materials leave the surface upon which they have been used gummy and sticky.

A water repellency test was used to compare the hydrophobicity of the material comprising the cleanup pad of the invention to other currently used materials. Water repellency is defined as the ability of a substrate to resist wetting by water or watery liquids. The test method used was designed to provide a simple measurement of aqueous stain resistance. The results obtained from this test depend primarily on the resistance to wetting (water repellency) of the fibers in the substrate, and not upon the construction of the substrate.

To determine the Water Repellency Value, each substrate's resistance to wetting by a selected series of water and isopropyl alcohol mixtures is measured. The series of mixtures ranges from 100% water to 100% isopropyl alcohol, with the test liquid number increasing as the percentage of water decreases and the percentage of isopropyl alcohol increases. The Water Repellency Value of a substrate is the highest numbered test liquid which will not wet the substrate within a period of thirty seconds, evaluated at 20° C. Table 1 gives the number and composition of each mixture in the selected series.

TABLE 1

| STANDARD TEST LIQUIDS | |
|---|---|
| Test Liquid | Percent Composition of Test Liquid |
| W | 100 Water |
| 1 | 90/10 Water/Isopropyl Alcohol |
| 2 | 80/20 Water/Isopropyl Alcohol |
| 3 | 70/30 Water/Isopropyl Alcohol |
| 4 | 60/40 Water/Isopropyl Alcohol |
| 5 | 50/50 Water/Isopropyl Alcohol |
| 6 | 40/60 Water/Isopropyl Alcohol |
| 7 | 30/70 Water/Isopropyl Alcohol |
| 8 | 20/80 Water/Isopropyl Alcohol |
| 9 | 10/90 Water/Isopropyl Alcohol |
| 10 | 100 Isopropyl Alcohol |

Substrates were rated as a pass/fail of the appropriate test liquid. Resistance to wetting is indicated by a clear drop with a high contact angle. Wetting is normally evidenced by a darkening of the substrate at the liquid-substrate interface.

TABLE 2

| Material | W | Liquid 1 | Liquid 2 | Liquid 3 | Liquid 4 |
|---|---|---|---|---|---|
| Cellulose | Y | | | | |
| Cotton | Y | | | | |
| Rayon/polyester blend | Y | | | | |
| polypropylene | N | N | N | N | Y |

Table 2 shows the results of the water repellency test for various materials. The Y's and N's in Table 2 denote if the material was wetted by the liquid (Y) or was not wetted by the liquid (N).

Preferably, the material used to form the cleanup pad of the invention has a Water Repellency Value of no less than 3.

Other liquids of varying surface tensions were also used to evaluate the sorbency properties of material comprising the pad of the invention. Surface tension is typically measured at 20° C., and reported in dynes per centimeter (dynes/cm). The material comprising the cleanup pad of the invention absorbed quinoline and, but did not absorb water, glycerol, formamide or ethylene glycol.

TABLE 3

| Liquid | Surface Tension | Sorbence by clean-up pad |
| --- | --- | --- |
| Water | 73.05 | N |
| Glycerol | 63.4 | N |
| Formamide | 58.2 | N |
| ethylene glycol | 47.7 | N |
| quinoline | 45 | Y |
| benzyl alcohol | 39 | Y |
| pyridine | 38 | Y |

The results of Table 3 indicate that material of the cleanup pad will preferably absorb liquids with a surface tension less than that of ethylene glycol, 47.7 dynes/cm. Thus, in a preferred embodiment, the material used to form the cleanup pad of the invention absorbs only those substances with a surface tension of less than 47.7 dynes/cm, and more preferably less than 40 dynes/cm.

Random orientation of the fibers in the web may be preferable to a patterned orientation. Although the patterned orientation has a smaller surface area and thus sorbs less in bulk, the key parameter is the wetting of the fibers of the pad by the resin. The resin wets the fibers at the cement-fiber interface. Resin containing filler particles becomes entrapped in the interstitial spaces. Thus, the construction is not as critical as the affinity of the fibers for the resin. That is, the material needs to have some minimum bulk absorbency, but the loft of the pad is provided to give the pad sufficient thickness so that it can be gripped by a cotton pliers.

Any process that results in a material with suitable physical properties may be used, although a preferred process for making the material from which the pads are formed is a web made by a blown microfiber process. The pad should possess sufficient integral strength to resist break-up even when saturated with fluids. Optionally, reinforcing fibers may also be incorporated to improve the strength characteristics of the resulting article.

In a preferred embodiment, the pads are die cut from a web into 9.5 millimeter disks. The disks preferably have a thickness of between 1 and 2 millimeters. Other sizes and shapes of material will also suffice. Any cutting means that cuts the material cleanly without leaving loose fibers may be utilized. Approximately 2–3 pads per crown will normally be sufficient to remove excess resin-containing cement.

The sorbent pads of the invention may be used in a variety of cleanup procedures, such as those for the placement of crowns, bridges, inlays, outlays, or veneers. The cleanup pad of the invention will generally provide efficient cleanup of any dental resin-based materials. The dental resin-containing materials may be unfilled or filled. If filled, any suitable dental filler or combination of fillers well known to those skilled in the art may be incorporated into the resin system. Examples of unfilled dental resin-containing materials include adhesives and sealants while examples of filled dental resin-containing materials include cements and composites.

Dental resins are typically derivatives of acrylate or methacrylate compounds. Examples of dental resins include, but are not limited to, acrylate, methacrylate, urethane and epoxy resins and mixtures and derivatives thereof. Commonly utilized dental resins include 2,2-bis[4-(2-hydroxy-3-methacryloxypropoxy)phenyl]propane ("Bis-GMA"), triethyleneglycol dimethacrylate ("TEGDMA"), ethoxylated bisphenol A dimethacrylate, 2-hydroxyethyl methacrylate, polyethyleneglycol dimethacrylate, urethane dimethacrylate, and mixtures thereof.

The dental resin-containing materials may be unfilled or filled. If filled, any suitable dental filler or combination of fillers well known to those skilled in the art may be incorporated into the resin system. Examples of unfilled dental resin-containing materials include adhesives and sealants while examples of filled dental resin-containing materials include cements and composites.

The cleanup pad of the invention may also be used on models in the dental laboratory to remove excess resin-containing material. It is not as critical in this use that the material be hydrophobic as when the pad is used in the moist environment of the oral cavity.

The material used to make the pads of the invention may also be drawn into a string, to be used as a floss. Such a floss is particularly useful for removing resin from interproximal spaces.

EXAMPLES

The invention will be further explained by the following illustrative examples which are intended to be non-limiting.

Example 1

Manufacture of the Cleanup Pad

The cleanup pads can be made from a jumbo roll (91.4 cm" dia.×48.3 cm" width) of polypropylene blown microfiber. This roll is fed into a slitter and reduced to 51 cm" dia.×5 cm" width. The reduced roll is fed into a rotary die stamper setup with dies in the range of 0.64 cm" to 1.3 cm' in diameter. This process yields a finished pad free of strands on the perimeter due to cold welding of the filaments during the die stamping process.

Example 2

Resin Cement Cleanup of a Luted Crown

Immediately after seating a crown, (PFM, all porcelain, metal, composite), initiate cleanup. Excess resin cement (a filled Bis-GMA/TEGDMA cement) is removed interproximally with dental floss (available from Johnson & Johnson Consumer Products Inc., Skillman, N.J.). Facial and lingual surfaces are cleaned with the cleanup pad of Example 1 (disk of approximately 9.5 millimeters diameter and approximately 2.5 millimeters thickness). The pad is gripped with a cotton pliers (Miltex Instrument Co., Lake Success, N.Y.) and wiped across the facial surface of the crown, at the margin of the crown and the tooth, and any other place where excess resin is present. This process is repeated on the lingual crown surface to complete the cleanup procedure.

Example 3

Resin Cement Cleanup: Cleanup Pads of Example 1 Compared to Competitive Materials The efficacy of the cleanup pads of Example 1 was demonstrated by the following test. A small mount (½ gram) of resin luting cement (3M Scotchbond™ Resin Cement) was extruded as a film about ½ millimeter thick onto a glass microscope slide (from VWR Scientific Inc., San Francisco, Calif. 94120, catalogue #4800-025). The slide with the extruded resin film was immersed in a petri dish of water. While immersed in the water, the resin was wiped from the slide with a disk of the cleanup material.

The slide was then examined for evidence of residual resin. The cleanup material of the invention resulted in a clean surface. The same procedure was performed using NuGauze™ sponge from Johnson & Johnson, which resulted in noticeable amounts of resin left on the slide.

Various modifications and alterations of this invention will become apparent to those skilled in the art without departing from the scope and spirit of this invention.

What is claimed is:

1. A method for selectively sorbing substantially hydrophobic dental resins comprising
   a) applying a substantially hydrophobic dental resin to a dental surface in need of treatment; and
   b) removing excess hydrophobic dental resin from said dental surface by wiping said excess resin with a dental article for use in selectively sorbing substantially hydrophobic dental resins from an environment containing aqueous fluids, said article comprising a material having a Water Repellency Value greater than 1.

2. The method of claim 1, wherein said dental surface is in the oral cavity.

3. The method of claim 1, wherein said material is a nonwoven web.

4. The method of claim 1, wherein said material is a woven web.

5. The method of claim 1, wherein said material is attached to an applicator.

6. The method of claim 1, wherein said material is used as a dental floss.

7. The method of claim 1, wherein said material absorbs liquids having a surface tension less than 47.7 dynes/cm.

8. The method of claim 1, wherein said material absorbs liquids having a surface tension less than 40 dynes/cm.

9. The method of claim 1, wherein said material is selected from the group consisting of polypropylene and polyethylene, and mixtures thereof.

10. The method of claim 1, wherein said article has a sheet-like configuration having an overall size of less than about 250 cm$^2$.

11. The method of claim 1, wherein said article has a sheet-like configuration having an overall size of less than about 25 cm$^2$.

12. A method for cementing a crown in place, comprising the steps of
   a) placing a substantially hydrophobic cement into a crown;
   b) seating said crown on a prepared tooth with excess cement exuding from the margins of said crown; and
   c) removing said excess cement from surfaces of said crown with a dental article for use in selectively sorbing substantially hydrophobic dental resins from an environment containing aqueous fluids, said article comprising a material having a Water Repellency Value greater than 1.

* * * * *